United States Patent [19]
Vanderberg et al.

[11] Patent Number: 6,077,704
[45] Date of Patent: Jun. 20, 2000

[54] HETEROGENEOUS WASTE PROCESSING

[75] Inventors: Laura A. Vanderberg; Nancy N. Sauer; James R. Brainard; Trudi M. Foreman; John L. Hanners, all of Los Alamos, N. Mex.

[73] Assignee: The Regents of the University of California, Los Alamos, N. Mex.

[21] Appl. No.: 08/858,203

[22] Filed: May 9, 1997

[51] Int. Cl.[7] ............................. C12S 13/00; B09C 1/10
[52] U.S. Cl. ...................................... 435/262.5; 435/262
[58] Field of Search .................. 435/262.5, 262, 435/274, 276, 277, 278, 256.6, 256.7; 588/205, 223, 231, 236; 210/603, 606, 609; 241/DIG. 38

[56] References Cited

U.S. PATENT DOCUMENTS

| | | |
|---|---|---|
| 4,293,334 | 10/1981 | Drobot et al. . |
| 4,409,329 | 10/1983 | Silver . |
| 5,160,636 | 11/1992 | Gilles et al. . |
| 5,326,477 | 7/1994 | Fugua et al. . |
| 5,348,871 | 9/1994 | Scott et al. . |
| 5,362,397 | 11/1994 | Cyr . |
| 5,376,539 | 12/1994 | Furuhashi et al. . |
| 5,506,123 | 4/1996 | Chieffalo et al. . |
| 5,518,920 | 5/1996 | Stewart et al. . |

FOREIGN PATENT DOCUMENTS

| | | |
|---|---|---|
| 47 17 515 | 12/1992 | Germany . |
| 41 41 889 | 6/1993 | Germany . |

OTHER PUBLICATIONS

Warhurst et al. "Production of Catechols and Muconic Acids . . . " Biotechnology Letters. vol. 16, No. 5 (May 1994), pp. 513–516.

Malachowsky et al. "Aerobic Mineralization of Trichloroethylene . . . " Appl. Environ. Microbiol. vol. 60, No. 2 (Feb. 1994), pp. 542–548.

Vanderberg–Twary et al. "Integrated chemical/biological treatment of a paint stripper mixed waste . . . " Mixed Waste, Proc. Bienn. Symp., 3rd. (1995), pp. 11.7.1–11.7.6.

Vanderberg–Twary et al. "Bioremediation of environmental contaminants by soil mycobacteria." Proc. ERDEC Sci. Conf. Chem. Biol. Def. Res. (1996),pp. 137–141.

*Primary Examiner*—William H. Beisner
*Attorney, Agent, or Firm*—Bruce H. Cottrell

[57] ABSTRACT

A combination of treatment methods are provided for treatment of heterogeneous waste including: (1) treatment for any organic compounds present; (2) removal of metals from the waste; and, (3) bulk volume reduction, with at least two of the three treatment methods employed and all three treatment methods emplyed where suitable.

17 Claims, 2 Drawing Sheets

HETEROGENEOUS WASTE PROCESSING

This invention is the result of a contract with the United States Department of Energy (Contract No. W-7405-ENG-36).

FIELD OF THE INVENTION

The present invention relates to the processing of heterogeneous waste, i.e., waste containing, e.g., volatile organic compounds, hydrocarbons, metals, and/or bulk materials.

BACKGROUND OF THE INVENTION

Generally, the presence of bulk materials in a heterogeneous waste mixture prevents treatability of the waste stream by any single, established technology. Current storage and disposal methods are both costly and in violation of laws governing the storage of mixed waste.

In previous practices, some facilities have generated large quantities of wastes which contain both a hazardous chemical component or components and a radioactive component. This type of waste is referred to as a mixed waste. Mixed wastes are still generated by some facilities, e.g., those involved in activities such as decontamination and decommissioning of actinide processing operations. One class of mixed wastes is generated when paint is stripped from surfaces contaminated with an actinide such as plutonium. Such a waste typically includes a paint stripper such as methylene chloride together with other solvents, lead- and cellulose-based paint, bulk materials such as cheesecloth rags, cardboard and cotton labcoats, and in some cases, minor amounts of a radioactive component such as plutonium. As current storage practices are expensive, if not unlawful under U.S. laws, and alternatives such as incineration have not gained general acceptance, the development of an environmentally benign, publicly acceptable solution has been sought.

An object of the present invention is a process for treating heterogeneous wastes such as mixed wastes whereby organic components such as volatile organic components and other hydrocarbons are removed or eliminated, contaminant toxic metals such as lead, chromium and the like are separated, and the volume of any bulk materials is reduced.

SUMMARY OF THE INVENTION

In the present invention, a combination of treatment methods are employed for treatment of heterogeneous waste. The treatment methods employed include: (1) treatment for any organic compounds present; (2) removal of metals from the waste; and, (3) bulk volume reduction. The present invention uses at least two of the three treatment methods and can employ all three where suitable.

DETAILED DESCRIPTION

Figure 1:
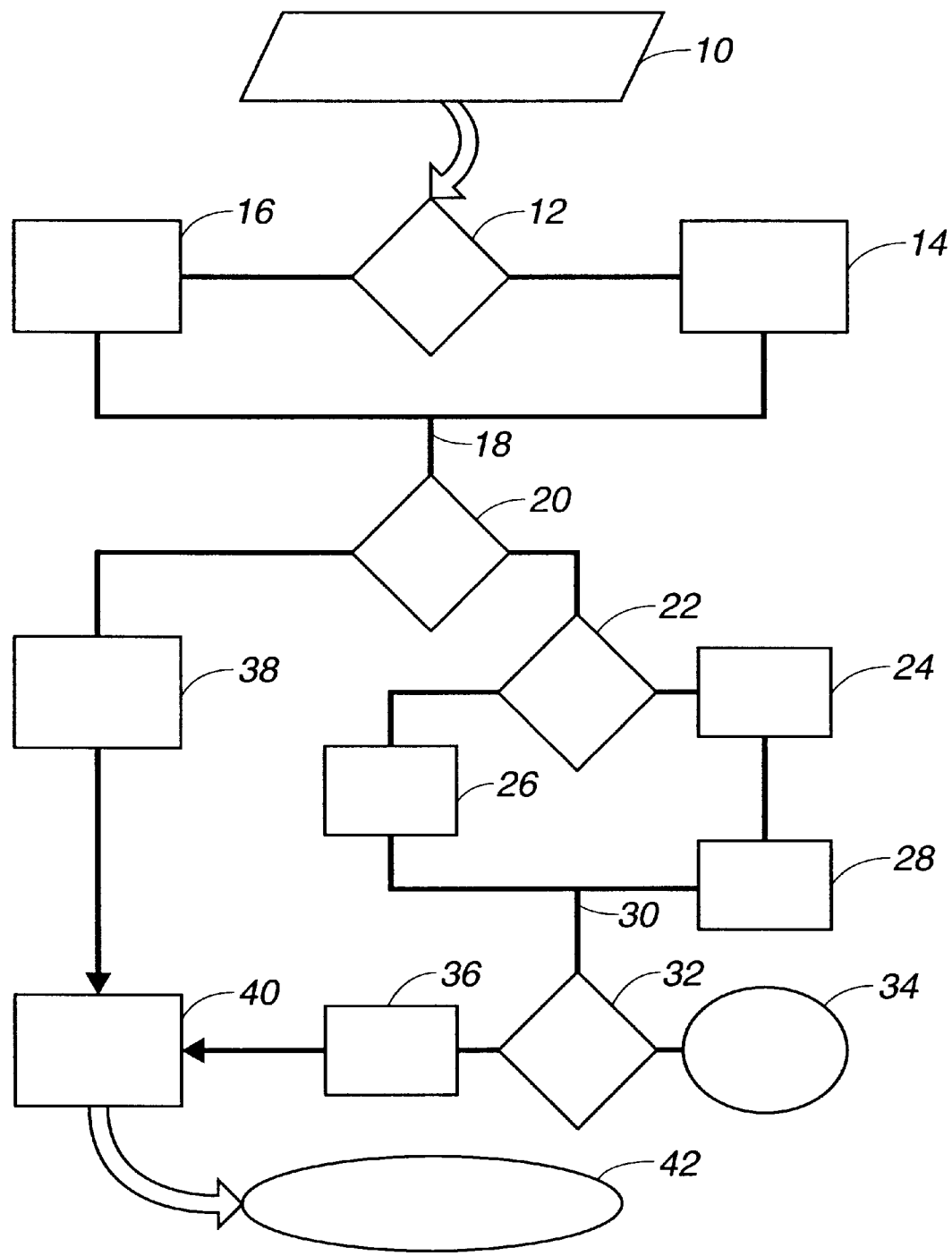
FIG. 1 shows a flow chart illustrating the process of the present invention.

In FIG. 1, a flow chart generally illustrating the present process is shown. A complex waste 10 is initially analyzed for volatile organic compounds (block 12).

When a particular waste contains volatile organic compounds (VOCs), a separate bioreactor 14 can be used to treat such materials. One inherent advantage to the bioremediation of solvents is the volatility of these organics. By employing a sparging bioreactor, the organics are volatilized from the waste material and swept into the bioreactor. Specific combinations of microbes present in the reactor can metabolize these hazardous organics completely to carbon dioxide and water. The harmless by-products can then be released into the atmosphere. The sparging bioreactor is mobile and can be remounted and reused a number of times. In cases where high levels of hazardous organics are present, the system can be set up in a recycle mode. Once effluent samples reach acceptable low levels, the system can then be vented into the open air.

The sparging bioreactor system minimizes volume because the biomass does not come in direct contact with contaminants other than the organic material. It also allows complex wastes to be treated effectively by separating the destructible organic components from the rest of the waste. A modular approach to such a bioreactor system allows the flexibility to tailor make waste treatment systems specific for many different waste streams.

For destruction of organics typical to paint strippers, two different microbes have been successfully employed in a defined consortium. Such microbes can both utilize hydrocarbons as sole sources of carbon and energy and are selected for their ability to grow on at least one of the common components in the organic components of the waste. *Hyphomycrobium sp.* strain DM-2 (ATCC 43129) degrades methanol and methylene chloride and *Rhodococcus rhodochrous* strain OFS (ATCC 29672) degrades toluene, acetone and other hydrocarbons. Both strains use their respective substrates for growth and no by-products accumulate.

Control of air flow rate through the gas lift loop bioreactor can be necessary. An optimum flow rate has been found to be about 5 standard cubic feet per hour (scfh) a rate whereat oxygen was not a limiting factor. At lower flow rates, biodegradation was somewhat inhibited, presumably due to a limitation of oxygen. At higher flow rates, the microbes were aerosolized out of the liquid in the reactor thereby preventing biodegradation of the water soluble components.

*R. rhodochrous* has also been successfully employed in an activated sludge sanitary waste treatment regimen to mitigate the toxicity caused by influent industrial type wastes. In such situations, the *R. rhodochrous* can consume the influent industrial type wastes such as acetone.

Other suitable bacterial cultures for VOC degradation can include the following: *Rhodococcus sp.* strain R-22 (ATCC 29671); *Mycobacterium vaccae* strain JOB-5 (ATCC 29678); *Hyphomycrobium sp.* strain DM2 (ATCC 43129); *Mycobacterium convolutum* strain NPA1; *Mycobacterium rhodochrous* strain P101Y; *Rhodococcus rhodochrous* strain 7E1C (ATCC 19067); and, *Mycobacterium convolutum* strain B58.

When a particular waste does not contain volatile organic compounds (VOCs), the bioreactor can be bypassed and an in-barrel process 16 can be employed. Several different strains of hydrocarbon utilizers from known culture collections such as propane utilizer strain Sp2, propane utilizer strain Sp3, propane utilizer strain Sp4a, propane utilizer strain Y1 and *Nocardia asteroides* strain A23, can be used on waste free of VOCs. All such strains are hydrocarbon and gaseous hydrocarbon utilizers with several which grow on toluene, benzene and other aromatic compounds. These microbes are robust and can grow on nonsoluble hydrocarbons such as long chain hydrocarbons ($C_{12}$–$C_{40}$). They may be employed for destruction of nonvolatile organic compounds typical of other wastes.

Non-volatile organic compounds of general concern are those listed as hazardous by the United States Resource Conservation Recovery Act. Among particular non-volatile organic compounds of concern can be included aliphatic hydrocarbons, ketones, esters, halogenated, e.g., brominated or chlorinated hydrocarbons, and nitrated organic compounds such as typical explosive-type compounds.

Eventually the complex waste stream 18 is analyzed for metals (block 20). If metals are present, the effect of these metals on bacteria must be determined. A "micro" plate counting assay has been developed that determines the toxicity (block 22) of different concentrations of metals on selected bacteria. The toxicity of metals is an important consideration when designing the order of steps in the heterogeneous waste destruction process. The "micro" plate counting assay involves growing the particular bacterium on a substrate and then adding the particular metal at a predetermined concentration. The bacterium was allowed to grow for twenty-four hours and following a standard dilution series the results are compared to growth controls without the presence of the metals. In addition, degradation of solvents in the presence of metals can be monitored by GC-FID and GC-MS to identify toxicity problems.

When no metals are present, there is no concern with adding microbes directly to containers containing waste. Organics will be destroyed and bulk materials will be minimized by liquefication by fungal cellulases (described in more detail in section on bulk volume reduction.)

If metals are found toxic to a particularly desired bacterium, the process will be set up so that metals are either (a) removed (block 24) by chelation, e.g., with ion exchange resins, or with suitable enzymatic chelators such as extracellular enzymes secreted by *Trichoderma reesei* strain QM 9414, prior to organics destruction in the container, or (b) left in the container for later removal, e.g., by such chelators, if organics can be destroyed in a bioreactor.

If metals are not found toxic to a particularly desired bacterium, simultaneous organics destruction, in a container, and metals removal may be done in the container in a chemical-biological process (block 26).

When a particular waste contains radioactive components (radwaste), remaining radwaste can be processed (block 34) according to the appropriate procedures as well known to those skilled in the art.

If no radioactive components are present in the particular waste, the metals can be recovered.

For bulk volume reduction (block 40) the following procedure can be followed. In the bioreactor setup, bulk volume reduction can be performed simultaneously with organics destruction. Pretreatment of bulk materials (such as cheesecloth, cotton labcoats, cardboard, and paper) is done to reduce the size of the bulk materials. This size reduction can be generally accomplished by ball-milling, chopping, or by a combination of size reducing techniques. Generally, ball-milling alone for a period of from about 3 to 5 days has been found most effective. Following pretreatment, an acetate buffer, pH 4.8, was added to the container along with previously prepared crude enzyme (a crude extract of extracellular enzymes secreted by *Trichoderma reesei* strain QM 9414). The enzyme converted cellulose to sugars and mobilizes metals from paint chips or particles. The paint was reduced or degraded to a fine white powder in this process and all pigment was released as metals into the solution. Released metals, sugars, and free enzymes were removed by ultrafiltration through an Amicon concentrator. This resulted in a concentrated free enzyme retained by the filter that is recycled into the bulk minimization. Sugar syrup containing metals passed through the filter. Suitable chelators can then be employed to chelate and remove metals leaving a liquid sugar syrup that can be used as a harmless feed stock for other microbes.

Mutant strains of the *Trichoderma reesei* strain QM 9414 have been generally found to be most preferable in this process.

The types of input (or starting material) for heterogeneous waste processing (HWP) include the following: paint stripping wastes such as solvents, rags, metals, and radionuclides; petroleum wastes such as hydrocarbons, rags, and metals; soil and cleanup debris such as chlorinated solvents, sand, and soils; combustibles and filters such as paper, cloth, wood, radionuclides, and solvents; and metals plating wastes such as metals, and solvents.

With paint stripper heterogeneous waste including materials such as metals, VOCs, and bulk materials, a heterogeneous waste processing can be as follows.

Paint stripping waste can be initially characterized by sampling the barrel headspace for VOCs by gas chromatography-mass spectrometry (GC-MS) and gas chromatography-flame ionization detector (GC-FID), and pulling a bulk sample and running an EPA Toxicity Characteristic Leaching Procedure (TCLP) test with inductively coupled plasma (ICP) analysis for metals. Following characterization, the material is treated according to the HWP methodology.

Figure 2:
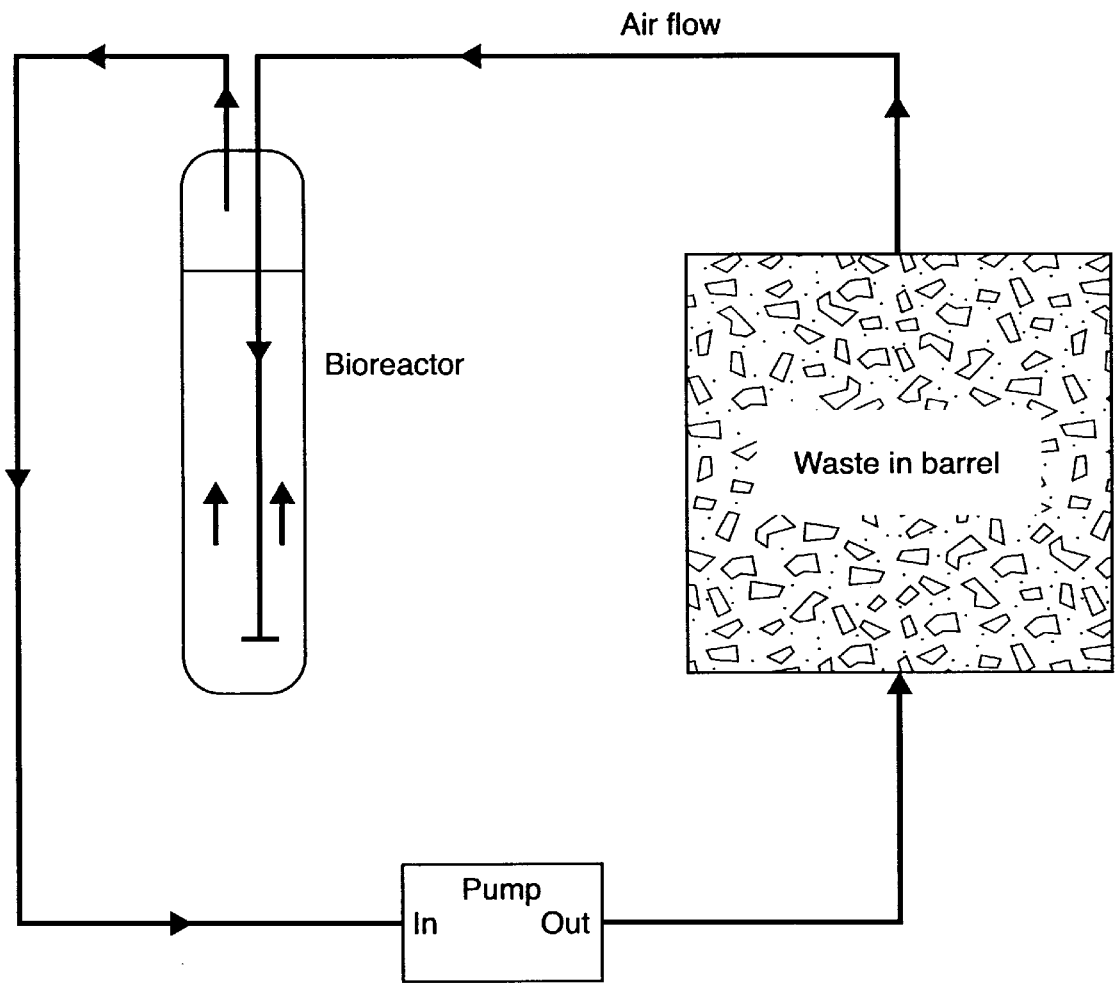
FIG. 2 shows a general view of the process with a bioreactor.

The presence of methanol, isopropanol, and methylene chloride can be typically anticipated in paint stripping wastes. The bioreactor is filled with 1 L minimal salts medium and concentrated washed cells. The reactor is hooked in line with the sealed air pump and the waste barrel shown in FIG. 2. The air flow can be set at 5 standard cubic feet per hour (scfh). Air is circulated through the waste barrel and into the bioreactor sweeping the VOCs into the bioreactor. Degradation of substrates can be monitored by sampling the liquid with a syringe and filtering the sample into 1.8 ml autosample vials. Samples can be analyzed by GC-FID in triplicate. When the influent air no longer contained VOCs (as determined by sampling the influent port air with a gas tight syringe) and the VOCs are depleted in the liquid, the bulk materials in the barrel can be pretreated by ball-milling.

The metals present in paint stripping waste are typically chromates ($Cr^{III}$ and $Cr^{VI}$) and lead (Pb). All three metals have been determined to be toxic to *Hyphomicrobium sp.* DM-2, and much less toxic to *R. rhodochrous* OFS. The toxicity problem led to the design of the bioreactor. Following pretreatment of bulk materials, acetate buffer of pH 4.8 is added to the barrel. The bioreactor can be hooked up again and air flow can serve as the oxygen source for the bacteria and mixing for the bulk materials reduction. After a suitable length of time, cellulase enzyme preparations can be added to the barrel. At that time, the oxygen supply is cut off and the materials mechanically stirred. Concurrently, any VOCs released by the pretreatment will be degraded by bacteria in the bioreactor.

Bulk volume reduction is accomplished by the action of extracellular fungal enzymes known as cellulases. These cellulases are a complex of different enzymes, notably an exo-cellulases (EC 3.2.1.91), endo-cellulases (EC 3.2.1.4), and beta-glucosidase (EC 3.2.1.21). Fungal exo-cellulase (EC 3.2.1.4) from *Trichoderma reesei* (ATCC 26921) can be purchased commercially from Sigma Chemical Co. for use in the bulk volume reduction. This commercial preparation works adequately. It has been found that a higher actvity crude enzyme (2 times the activity of commercially prepared cellulase) can be prepared in the following manner. *T reesei* QM 9414 (ATCC 26921) was grown in 1 L batches of a medium referred to as "M" (preparation shown below) with microcrystalline cellulose as a growth substrate. Levels of beta-glucosidase activity were monitored calorimetrically during growth of the fungus and when levels were highest, the fungal material was removed by centrifugation and the crude enzyme preparation was quick frozen in liquid nitrogen and maintained at −80° C. until use.

During the bulk reduction sequence, sugars were released into the buffer along with metals. Every 2–3 days, sugar levels were monitored calorimetrically and free metals were determined by ICP analysis. When sugar levels were high enough, they were harvested by ultrafiltration through a 10,000 molecular weight cutoff ultrafiltration unit from Amicon. During the ultrafiltration, free soluble enzyme (beta-glucosidase) was concentrated, and sugars and solublized metals were removed. The other portion of the cellulase enzyme complex remained bound to the cellulose. Beta-glucosidase was returned to the barrel along with additional acetate buffer. Replenishment of the beta-glucosidase is necessary and has been referenced as the most costly part of agricultural cellulose destruction. By recycling the enzyme, this problem was avoided. Metals were removed from the waste during this sugar reduction/enzyme recycle step. The metal-sugar-acetate buffer solution can be discarded or metals may be further recovered with suitable chelators leaving an acetate-sugar solution that may be used as a feedstock for other microbes. If radioactive metals are present, they may be chelated and sent to a radwaste treatment facility. In this manner, mixed waste can be separated into concentrated rad-metals and RCRA metals, effectively reducing the volume of waste that needs to be stored as mixed waste. The volume reduction of bulk materials requires little manpower and may be left at room temperature, unattended for extended periods of time. The length of time that this step continues depends upon the volume reduction desired.

The "M" Medium with 100 mM Buffer was prepared substantially in accordance with Labudova, I. and V. Farkas. 1983. Biochem. Biophys. Acta. 744: 135–140. The "M" Medium included the following:

| | | |
|---|---|---|
| 1.4 | g | $(NH_4)SO_4$ |
| 2.0 | g | $KH_2PO_4$ |
| 0.3 | g | Urea |
| 0.39 | g | $CaCl_2.2H_2O$ |
| 0.61 | g | $MgSO_4.7H_2O$ |
| 7.5 | g | Crystalline Cellulose |
| 1.0 | g | Protease Peptone (BactoPeptone) |
| 1 | ml | Tween 80 surfactant |

Preparation involved measuring the powders, adding 500 mL deionized $H_2O$, 243 ml Stock A (see below), and 257 ml Stock B (see below), then adding 1 ml trace metals solution and the Tween 80 surfactant. The pH is checked to make sure it is between 4.5 and 5.0.

200 mMBuffer*

Stock A: 200 mM Citric Acid 84 g Citric Acid.$H_2O$ in 2 liters deionized $H_2O$
10.206 g//finished medium Stock B: 400 mM Sodium Phosphate
113.57 g Sodium Phosphate, dibasic anhydrous in 21 deionized $H_2O$
14.594 g/l finished medium To make up 11 100 mM buffer, pH 5:

243 ml Stock A
257 ml Stock B
500 ml deionized $H_2O$

| | |
|---|---|
| 0.500 g | $FeSO_4.7H_2O$ |
| 0.160 g | $MnSO_4.H_2O$ |
| 0.140 g | $ZnSO_4.7H_2O$ |
| 0.366 g | $CoCl_2.6H_2O$ |

Make up in 100 ml deionized $H_2O$.

*Italics indicate modifications from the cited reference used for improved cellulase activity.

In a related development involving *Rhodococcus rhodochrous* strain OFS (ATCC 29672), it was found that this strain oxidizes chemical species such as toluene, benzene and phenol yielding various chemical products including benzyl alcohol, benzaldehyde, benzoate, para-cresol, 4-methylcatechol, cis-dihydrodiol, and 3-methylcatechol. Other products such as dihydroxybenzoic acid may be prepared using combinations of the pathways in these reactions.

*Rhodococcus rhodochrous* strain OFS was grown on AM-1 minimal media agar plates supplied with toluene vapors in a dessicator and incubated at 30° C. Liquid cultures of the OFS contained 200 milliliters of AM-1 with toluene supplied as vapor from a one liter flask equipped with a center well. Cultures were placed in a shaker at 30° C. and grown to log phase. Purity of these cultures were maintained by isolation streaking and Gram staining. Analysis by GC-MS indicated the formation of products including benzyl alcohol, benzaldehyde, benzoate, para-cresol, 4-methylcatechol, cis-dihydrodiol, and 3-methylcatechol. Thus, it can be seen that *Rhodococcus rhodochrous* strain OFS can be used for the oxidation of aromatic compounds such as toluene and can form numerous resultant products. While not wishing to be bound by the following explanation, various pathways are believed to be operating in the oxidation of the aromatic compounds.

What is claimed is:

1. A process of treating heterogeneous waste including organic compounds and a volume of bulk materials comprising:

initially treating said heterogeneous waste so as to eliminate said organic compounds, wherein said organic compounds are selected from the group consisting of volatile organic compounds and non-volatile organic compounds with the proviso that where said organic compounds are volatile organic compounds, said treating heterogeneous waste so as to eliminate said organic compounds is by contact of said volatile compounds with at least one microbe adapted for degradation of said volatile organic compounds as a sole source of carbon and energy and where said organic compounds are non-volatile organic compounds, said treating heterogeneous waste so as to eliminate said organic compounds is by contact of said nonvolatile compounds with at least one microbe adapted for degradation of said non-volatile organic compounds as a sole source of carbon and energy; and, treating said heterogeneous waste so as to reduce the volume of bulk materials.

2. The process of claim 1 wherein said at least one microbe adapted for degradation of said volatile organic compounds includes at least one microbe adapted for degradation of said volatile organic compounds selected from the group consisting of methanol and methylene chloride, and at least one microbe adapted for degradation of volatile organic compounds selected from the group consisting of toluene and acetone.

3. The process of claim 1 wherein said at least one microbe adapted for degradation of said non-volatile organic compounds as a sole source of carbon and energy includes at least one microbe adapted for degradation of said non-volatile organic compounds selected from the group consisting of aliphatic hydrocarbons, ketones, esters, halogenated hydrocarbons, and nitrated organic compounds.

4. The process of claim 1 wherein said treating said heterogeneous waste so as to eliminate said volatile organic compounds is conducted within a sparging bioreactor.

5. The process of claim 1 wherein said treating said heterogeneous waste so as to reduce the volume of bulk materials includes a pretreatment by size reduction of said bulk materials, followed by contact of said bulk materials for a sufficient time with an extracellular fungal enzyme.

6. A process of treating heterogeneous waste including organic compounds and metals comprising:

initially treating said heterogeneous waste so as to eliminate said organic compounds, wherein said organic compounds are selected from the group consisting of volatile organic compounds and non-volatile organic compounds with the proviso that where said organic compounds are volatile organic compounds, said treating heterogeneous waste so as to eliminate said organic compounds is by contact of said volatile compounds with at least one microbe adapted for degradation of said volatile organic compounds as a sole source of carbon and energy and where said organic compounds are non-volatile organic compounds, said treating heterogeneous waste so as to eliminate said organic compounds is by contact of said non-volatile compounds with at least one microbe adapted for degradation of said non-volatile organic compounds as a sole source of carbon and energy; and, treating said heterogeneous waste so as to separate the metals.

7. The process of claim 6 wherein said separating of metals is by chelation.

8. The process of claim 7 wherein said chelation of metals follows treatment with an extracellular fungal enzyme whereby said metals are solubilized.

9. The process of claim 6 wherein said at least one microbe adapted for degradation of said volatile organic compounds includes at least one microbe adapted for degradation of said volatile organic compounds selected from the group consisting of methanol and methylene chloride, and at least one microbe adapted for degradation of volatile organic compounds selected from the group consisting of toluene and acetone.

10. The process of claim 6 wherein said at least one microbe adapted for degradation of said non-volatile organic compounds as a sole source of carbon and energy includes at least one microbe adapted for degradation of said non-volatile organic compounds selected from the group consisting of aliphatic hydrocarbons, ketones, esters, halogenated hydrocarbons, and nitrated organic compounds.

11. A process of treating heterogeneous waste including organic compounds, metals and a volume of bulk materials comprising:

initially treating said heterogeneous waste so as to eliminate said organic compounds, wherein said organic compounds are selected from the group consisting of volatile organic compounds and non-volatile organic compounds with the proviso that where said organic compounds are volatile organic compounds, said treating heterogeneous waste so as to eliminate said organic compounds is by contact of said volatile compounds with at least one microbe adapted for degradation of said volatile organic compounds as a sole source of carbon and energy and where said organic compounds are non-volatile organic compounds, said treating heterogeneous waste so as to eliminate said organic compounds is by contact of said non-volatile compounds with at least one microbe adapted for degradation of said non-volatile organic compounds as a sole source of carbon and energy;

treating said heterogeneous waste so as to separate the metals; and, treating said heterogeneous waste so as to reduce the volume of bulk materials.

12. The process of claim 11 wherein said at least one microbe adapted for degradation of said volatile organic compounds includes at least one microbe adapted for degradation of said volatile organic compounds selected from the group consisting of methanol and methylene chloride, and at least one microbe adapted for degradation of volatile organic compounds selected from the group consisting of toluene and acetone.

13. The process of claim 11 wherein said at least one microbe adapted for degradation of said non-volatile organic compounds as a sole source of carbon and energy includes at least one microbe adapted for degradation of said non-volatile organic compounds selected from the group consisting of aliphatic hydrocarbons, ketones, esters, halogenated hydrocarbons, and nitrated organic compounds.

14. The process of claim 11 wherein said separating of metals is by chelation.

15. The process of claim 14 wherein said chelation of metals follows treatment with an extracellular fungal enzyme whereby said metals are solubilized.

16. The process of claim 11 wherein said treating said heterogeneous waste so as to reduce the volume of bulk materials includes a pretreatment by size reduction of said bulk materials, followed by contact of said bulk materials for a sufficient time with an extracellular fungal enzyme.

17. A process of oxidizing toluene to form a mixture of oxidized products comprising contacting toluene with *Rhodococcus rhodochrous* strain OFS (ATCC 29672) to form a mixture of oxidized products, said products selected from the group consisting of benzyl alcohol, benzaldehyde, benzoate, para-cresol, 4-methylcatechol, cis-dihydrodiol, 3-methylcatechol and dihydroxybenzoic acid.

* * * * *